United States Patent
Kirkland

(10) Patent No.: US 9,868,732 B2
(45) Date of Patent: Jan. 16, 2018

(54) PROCESS OF SYNTHESIZING 2-BROMO-LSD

(71) Applicant: Justin Kirkland, Champaign, IL (US)

(72) Inventor: Justin Kirkland, Champaign, IL (US)

( * ) Notice: Subject to any disclaimer, the term of this patent is extended or adjusted under 35 U.S.C. 154(b) by 0 days.

(21) Appl. No.: 14/990,219

(22) Filed: Jan. 7, 2016

(65) Prior Publication Data

US 2016/0237080 A1    Aug. 18, 2016

Related U.S. Application Data

(60) Provisional application No. 62/101,278, filed on Jan. 8, 2015.

(51) Int. Cl.
*C07D 457/06* (2006.01)
*C07D 457/00* (2006.01)

(52) U.S. Cl.
CPC .................... *C07D 457/06* (2013.01)

(58) Field of Classification Search
CPC ............................ C07D 471/06; C07D 457/06
USPC ....................................... 546/67, 69
See application file for complete search history.

(56) References Cited

U.S. PATENT DOCUMENTS 4,609,731 A * 9/1986 Jurgec ................. C07D 457/04
  544/236
8,895,743 B2 * 11/2014 Wu ...................... C07D 457/06
  546/67

OTHER PUBLICATIONS

TiHKAL "Acid, Lersergic . . . " p. 1-7, transform press (1997).*
Hempel et al. "Preparation of new . . . " CA107:40178 (1986).*
Exhibit I, p. 1-11 (2017).*

* cited by examiner

*Primary Examiner* — Charanjit Aulakh
(74) *Attorney, Agent, or Firm* — Charney IP Law LLC; Thomas M. Finetti

(57) ABSTRACT

A process of synthesizing 2-bromo-LSD or a salt or hydrate thereof comprising the steps of reacting methylergometrine with a brominating agent to produce [(1S)-1-(Hydroxymethyl)propylamino][(6aR,9R)-5-bromo-7-methyl-4,7-diaza-4,6,6a,7,8,9-hexahydroacephenanthrylen-9-yl]formaldehyde as a first intermediate, and then hydrolyzing [(1S)-1-(Hydroxymethyl)propylamino][(6aR,9R)-5-bromo-7-methyl-4,7-diaza-4,6,6a,7,8,9-hexahydroacephenanthrylen-9-yl]formaldehyde to yield bromo-lysergic acid as a second intermediate, wherein bromo-lysergic acid is then amidated to yield 2-bromo-LSD or a salt or hydrate thereof.

1 Claim, 1 Drawing Sheet

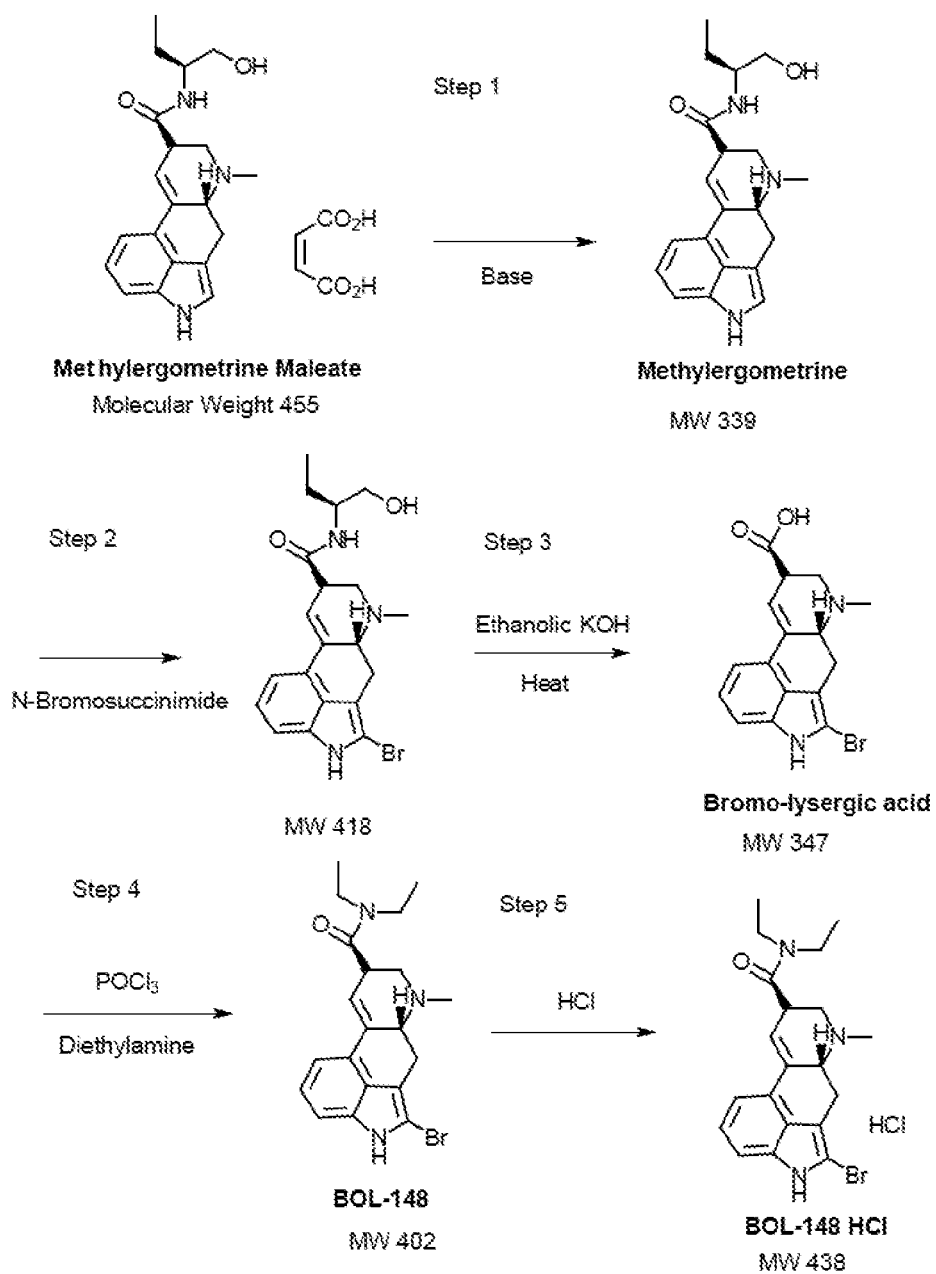
SCHEME 1

PROCESS OF SYNTHESIZING 2-BROMO-LSD

CROSS REFERENCE TO RELATED APPLICATIONS

The present application claims the benefit of the filing date of U.S. Provisional Patent Application 62/101,278, filed Jan. 8, 2015, the disclosure of which is hereby incorporated by reference herein in its entirety.

BACKGROUND OF THE DISCLOSURE

The synthesis of BOL-148 in the United States and many other countries is plagued with a handful of regulatory and chemistry issues. The first synthesis of 2-Bromo-LSD (BOL-148) comprised reacting 13.2 grams of N-bromosuccinimide (in 400 mL dioxane) with 1.2 liters of dioxane containing 25 grams of LSD. This gave 11 grams of crude product, which had to be recrystallized. The radioactive synthesis uses effectively elemental bromine, and provided yields ranging from 5 to 15%.

LSD is a schedule one drug in the United States and beginning in 1968 the United Nations Economic and Social Council (ECOSOC) passed a resolution calling on nations to limit the use of such drugs to scientific and medical purposes and to impose import and export restrictions. In accordance with the Convention on Psychotropic Substances of 1971, the International Narcotics Control Board listed LSD as Schedule 1 for United Nations member countries. Additionally, in 1988 the United Nations listed Ergometrine, Ergotamine, and Lysergic Acid under table 1 as precursors. Furthermore, the United States DEA covers Egonovine and Ergocristine as List 1 precursors.

The above regulations contribute to the overhead costs, regulatory resources, and additional expenses and permitting depending on the route chosen to manufacture BOL-148.

It would be beneficial to develop a synthetic method which overcomes these and other issues. Indeed, it would be beneficial to develop a method which eliminates any registration, importation permits, and/or controlled substance handling permits. It would also be beneficial to be able to develop a synthetic strategy that utilizes starting materials that are cost effective, readily available, and unregulated in use.

BRIEF SUMMARY OF THE DISCLOSURE

In one aspect of the present disclosure is a method of synthesizing 2-bromo-LSD without the use of any controlled or regulated starting materials or intermediates. In some embodiments, is a method of synthesizing 2-bromo-LSD without using one of ergometrine, ergotamine, Lysergic Acid, or LSD as a starting material.

In another aspect of the present disclosure is a method of synthesizing 2-bromo-LSD from methylergometrine or a salt or hydrate thereof.

In yet another aspect of the present disclosure is a method of synthesizing 2-bromo-LSD from bromo-lysergic acid or a salt or hydrate thereof.

In yet another aspect of the present disclosure is a method of synthesizing 2-bromo-methylergometrine or [(1S)-1-(Hydroxymethyl)propylamino][(6aR,9R)-5-bromo-7-methyl-4,7-diaza-4,6,6a,7,8,9-hexahydroacephenanthrylen-9-yl]formaldehyde from methylergometrine or a salt or hydrate thereof.

In yet a further aspect of the present disclosure is a method of synthesizing bromo-lysergic acid from [(1S)-1-(Hydroxymethyl)propylamino][(6aR,9R)-5-bromo-7-methyl-4,7-diaza-4,6,6a,7,8,9-hexahydroacephenanthrylen-9-yl]formaldehyde.

In yet another aspect of the present disclosure is a process of synthesizing 2-bromo-LSD or a salt or hydrate thereof comprising the steps of reacting methylergometrine with a brominating agent to produce [(1S)-1-(Hydroxymethyl)propylamino][(6aR,9R)-5-bromo-7-methyl-4,7-diaza-4,6,6a,7,8,9-hexahydroacephenanthrylen-9-yl]formaldehyde as a first intermediate, and then hydrolyzing [(1S)-1-(Hydroxymethyl)propylamino][(6aR,9R)-5-bromo-7-methyl-4,7-diaza-4,6,6a,7,8,9-hexahydroacephenanthrylen-9-yl]formaldehyde to yield bromolysergic acid as a second intermediate, wherein bromo-lysergic acid is then amidated to yield 2-bromo-LSD or a salt or hydrate thereof.

In yet another aspect of the present disclosure is a process of synthesizing 2-bromo-LSD or a salt or hydrate thereof comprising the steps of reacting methylergometrine with N-bromosuccinimide to produce [(1S)-1-(Hydroxymethyl)propylamino][(6aR,9R)-5-bromo-7-methyl-4,7-diaza-4,6,6a,7,8,9-hexahydroacephenanthrylen-9-yl]formaldehyde as a first intermediate, and then reacting [(1S)-1-(Hydroxymethyl)propylamino][(6aR,9R)-5-bromo-7-methyl-4,7-diaza-4,6,6a,7,8,9-hexahydroacephenanthrylen-9-yl]formaldehyde with a base to yield bromo-lysergic acid as a second intermediate, wherein bromo-lysergic acid is then reacted with an acylating agent in the presence of an amine to yield 2-bromo-LSD or a salt or hydrate thereof.

BRIEF DESCRIPTION OF THE FIGURES

FIG. 1 provides a synthetic scheme for the synthesis of 2-Bromo-LSD.

DETAILED DESCRIPTION

As used herein, the singular terms "a," "an," and "the" include plural referents unless the context clearly indicates otherwise. Similarly, the word "or" is intended to include "and" unless the context clearly indicates otherwise.

The terms "comprising," "including," "having," and the like are used interchangeably and have the same meaning. Similarly, "comprises," "includes," "has," and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a device having components a, b, and c" means that the device includes at least components a, b and c. Similarly, the phrase: "a method involving steps a, b, and c" means that the method includes at least steps a, b, and c. Moreover, while the steps and processes may be outlined herein in a particular order, the skilled artisan will recognize that the ordering steps and processes may vary.

As used herein, the term "2-bromo-LSD" refers to (6aR, 9R)-5-bromo-N,N-diethyl-7-methyl-4,6,6a,7,8,9-hexahydroindolo[4,3-fg]quinoline-9-carboxamide, its salts, hydrates, or racemates thereof.

As used herein, the term "ambient temperature" refers to a temperature ranging from 20°-25° C.

Disclosed are processes for synthesizing 2-bromo-LSD.

Scheme 1

Step 1: Freebasing

With reference to Scheme 1, a salt of methylergometrine, such as the maleate salt, is basified at step 1 to yield methylergometrine as a free base. In some embodiments, step 1 is carried out in an aqueous solution, or in a solvent (e.g. a hydrocarbon solvent (including those containing sulfur, a halogenated solvent, or mixtures thereof). Suitable bases include those organic or inorganic weak bases known in the art. In some embodiments, bases include those selected from potassium carbonate, potassium bicarbonate, potassium hydroxide, sodium carbonate, sodium bicarbonate, sodium hydroxide. In some embodiments, mixtures of bases are used. In some embodiments, the pH of base utilized ranges from about 7 to about 14. In other embodiments, the pH of the base utilized ranges from about 7.1 to about 12.0.

In some embodiments, about 1.1 equivalents of base are used for each equivalent of methylergometrine salt. In other embodiments, between about 1.1 and 1.5 equivalents of base are used for each equivalent of methylergometrine salt.

In some embodiments, step 1 is carried out at ambient temperature. In other embodiments, step 1 is carried out at a temperature ranging from about 0° C. to about 100° C. In some embodiments, step 1 is carried under stirring. In some embodiments, step 1 is carried out for a period of time ranging from about 60 minutes to about 240 minutes. It is believed that the yield of step 1 ranges from about 30% to about 99%.

In some embodiments of the present disclosure, the starting material for the synthesis of 2-bromo-LSD is methylergometrine as a free base and thus the process to synthesize 2-bromo-LSD would start at step 2 of scheme 1.

Step 2: Bromination

Turning to step 2 of scheme 1, the methylergometrine is brominated. In some embodiments, methylergometrine is treated with N-bromosuccinimide to yield [(1S)-1-(Hydroxymethyl)propylamino][(6aR,9R)-5-bromo-7-methyl-4,7-diaza-4,6,6a,7,8,9-hexahydroacephenanthrylen-9-yl]formaldehyde. In some embodiments, about 1-2 equivalents of N-bromosuccinimide are used per equivalent of methylergometrine. In some embodiments, step 1 is carried out in an aqueous solution, or in a solvent (e.g. a hydrocarbon solvent (including those containing sulfur, a halogenated solvent, or mixtures thereof).

In other embodiments, bromination of methylergometrine may be carried out with elemental bromine. In other embodiments, bromination of methylergometrine may be carried out by first lithiating methylergometrine and then treating the resulting intermediate with 1,2-dibromotetrachloroethane. Other methods of bromination known to those of skill in the art may be used provided they produce [(1S)-1-(Hydroxymethyl)propylamino][(6aR,9R)-5-bromo-7-methyl-4,7-diaza-4,6,6a,7,8,9-hexahydroacephenanthrylen-9-yl]formaldehyde.

In other embodiments, the brominating reagent may be selected from, but not limited to, benzyltrimethylammonium tribromide, boron tribromide, 2-bromo-2-cyano-N,N-dimethylacetamide, N-bromoacetamide, bromotrichloromethane, N-bromophthalimide, pyridine bromide, tetrabutylammonium tribromide, dibromoisocyanuric acid, 1,2-dibromo-1,1,2,2-tetrachloroethane, bromotrichloromethane. The brominating agent may be in an aqueous solution or a solvent (e.g. a hydrocarbon-based solvent or a halogenated solvent).

In some embodiments, step 2 is carried out at ambient temperature. In other embodiments, step 1 is carried out at a temperature ranging from about 0° C. to about 100° C. In some embodiments, step 2 is carried under stirring. In some embodiments, step 2 is carried out for a period of time ranging from about 60 minutes to about 240 minutes. It is believed that the yield of step 2 ranges from about 30% to about 99%.

Step 3: Hydrolysis

Turning to step 3, [(1S)-1-(Hydroxymethyl)propylamino][(6aR,9R)-5-bromo-7-methyl-4,7-diaza-4,6,6a,7,8,9-hexahydroacephenanthrylen-9-yl]formaldehyde is hydrolyzed to produce bromo-lysergic acid. In some embodiments, [(1S)-1-(Hydroxymethyl)propylamino][(6aR,9R)-5-bromo-7-methyl-4,7-diaza-4,6,6a,7,8,9-hexahydroacephenanthrylen-9-yl]formaldehyde is treated with a base to yield bromo-lysergic acid. In some embodiments, [(1S)-1-(Hydroxymethyl)propylamino][(6aR,9R)-5-bromo-7-methyl-4,7-diaza-4,6,6a,7,8,9-hexahydroacephenanthrylen-9-yl]formaldehyde is treated with a strong base and a catalytic amount of heat. In some embodiments, the strong base is selected from sodium hydroxide or potassium hydroxide or another strong basifying agent. In one particular embodiment, the strong base is ethanolic potassium hydroxide. In other embodiments, 0.01 to 1.0M ethanolic potassium hydroxide is used. In other embodiments, 0.1 to 1.0M ethanolic potassium hydroxide is used. In some embodiments, about 1.1 equivalents of strong base are used for every equivalent of substrate. In some embodiments of step 3, heat is applied at a temperature between about 50° C. and about 100° C. In some embodiments, step 3 is carried under stirring. In some embodiments, step 3 is carried out for a period of time ranging from about 60 minutes to about 240 minutes. In some embodiments, the addition of ethanolic potassium hydroxide is carried out in step-wise addition at the same or different temperatures until the substrate is consumed. It is believed that the yield of step 3 ranges from about 30% to about 99%.

In other embodiments, [(1S)-1-(Hydroxymethyl)propylamino][(6aR,9R)-5-bromo-7-methyl-4,7-diaza-4,6,6a,7,8,9-hexahydroacephenanthrylen-9-yl]formaldehyde is treated with sodium nitrate and acetic acid to yield bromo-lysergic acid. In yet other embodiments, [(1S)-1-(Hydroxymethyl)propylamino][(6aR,9R)-5-bromo-7-methyl-4,7-diaza-4,6,6a,7,8,9-hexahydroacephenanthrylen-9-yl]formaldehyde is treated with triflic acid and methanol to yield bromo-lysergic acid.

In some embodiments, the hydrolysis step takes place in an aqueous solution. In other embodiments, the hydrolysis step takes place in a solvent (e.g. a hydrocarbon-based solvent or a halogenated solvent).

In some embodiments of the present disclosure, the starting material for the synthesis of 2-bromo-LSD (or its salt or hydrate thereof) is bromo-lysergic acid (free base or salt or hydrate) and thus the process to synthesize 2-bromo-LSD would start at step 4 of scheme 1.

Step 4: Amidation

Turning to step 4 of scheme 1, bromo-lysergic acid is converted to an amide. In some embodiments, bromo-lysergic acid is treated with any halogenating agent to provide for an acyl halide intermediate, where the acyl halide intermediate reacts with an amine to yield the desired amide, as known to those of skill in the art. Other halogenating agents include but are not limited to $SOCl_2$, $PBr_3$, PBr₅, BBr₃, PCl₃, and PCl₅. In some embodiments, bromo-lysergic acid is reacted with phosphoryl chloride in the presence of an amine. Any amine may be used provided it produces the desired amide. For example, diethylamine or dimethylamine may be used to produce an amide after the intermediate acyl halide is formed. Diethylamine is used to produce the desired 2-bromo-LSD but other derivatives and variants may be envisioned according to the particular amine utilized.

In some embodiments, the amidation step takes place in an aqueous solution. In other embodiments, the amidation step takes place in a solvent (e.g. a hydrocarbon-based solvent or a halogenated solvent).

To yield the desired end product, 2-bromoe-LSD or the salt or hydrate thereof, bromo-lysergic acid is treated with phosphoryl chloride and diethylamine. In some embodiments, about 1 equivalents of phosphoryl chloride are used for every equivalent of bromo-lysergic acid. In some embodiments, about 2 equivalents of diethylamine are used for every equivalent of bromo-lysergic acid. In some embodiments, a ratio of the amount of phosphoryl chloride to the amount of amine ranges from about 1:1 to about 1:3.

In other embodiments, amidation of bromo-lysergic acid is carried out in the presence of a peptide coupling agent, organic/inorganic base and an appropriate amine. Examples of suitable peptide coupling agents include, but are not limited to, carbamates, carbazates, EDC, DCC, PyBOP, TBTU, and HATU. In other embodiments, amidation of bromo-lysergic acid is carried out by acid or base catalyzed esterification with an appropriate alcohol at an elevated temperature (about 30° C. to about 150° C.) followed by de-esterification in the presence of an amine (such as diethylamine) at an elevated temperature (about 30° C. to about 100° C.)

In some embodiments, step 4 is carried out at ambient temperature. In some embodiments, step 4 is carried under stirring. In some embodiments, step 4 is carried out for a period of time ranging from about 2 minutes to about 180 minutes. It is believed that the yield of step 4 ranges from about 30% to about 99%.

Step 5: Freebasing

Turning to step 5 of scheme 1, the salt of 2-bromo-LSD is converted from the free base 2-bromo-LSD via acidification. In some embodiments, the acidification is carried out with an organic or inorganic acid. Examples of acids include HCl, tartaric acid, malic acid, maleic acid, methanesulfonic acid, succinic acid, fumaric acid. In some embodiments, the acidification is carried out at a pH ranging from about 1 to about 6. In one embodiment, HCL is utilized. In other embodiments, 0.01 to 1.0M HCl is utilized. In yet other embodiments, 0.1 to 1.0M HCl is utilized.

In some embodiments, step 5 is carried out at ambient temperature. In some embodiments, step 5 is carried under stirring. In some embodiments, step 5 is carried out for a period of time ranging from about 30 minutes to about 480 minutes. It is believed that the yield of step 4 ranges from about 20% to about 99%.

The resulting 2-bromo-LSD end product may be amorphous or crystalline and, if crystalline, may have any of a number of polymorphic forms.

In some embodiments, the overall yield is between about 0.16% and about 99%.

Although the disclosure herein has been described with reference to particular embodiments, it is to be understood that these embodiments are merely illustrative of the principles and applications of the present disclosure. It is therefore to understood that numerous modifications may be made to the illustrative embodiments and that other arrangements may be devised without departing from the spirit and scope of the present disclosure as defined by the appended claims.

The invention claimed is:

1. A process of synthesizing 2-bromo-LSD or a salt or hydrate thereof comprising the step of reacting bromo-lysergic acid with POCl₃, wherein a ratio of an amount of POCl₃ to an amount of bromo-lysergic acid ranges from about 1:1 to about 1:3.

* * * * *